(12) United States Patent
Beira

(10) Patent No.: US 10,864,052 B2
(45) Date of Patent: Dec. 15, 2020

(54) SURGICAL INSTRUMENT WITH ARTICULATED END-EFFECTOR

(71) Applicant: DistalMotion SA, Lausanne (CH)

(72) Inventor: Ricardo Daniel Rita Beira, Lausanne (CH)

(73) Assignee: Distalmotion SA, Epalinges (CH)

( * ) Notice: Subject to any disclaimer, the term of this patent is extended or adjusted under 35 U.S.C. 154(b) by 59 days.

(21) Appl. No.: 15/536,562

(22) PCT Filed: Dec. 18, 2015

(86) PCT No.: PCT/IB2015/002493
§ 371 (c)(1),
(2) Date: Jun. 15, 2017

(87) PCT Pub. No.: WO2016/097864
PCT Pub. Date: Jun. 23, 2016

(65) Prior Publication Data
US 2017/0367778 A1    Dec. 28, 2017

Related U.S. Application Data

(60) Provisional application No. 62/094,077, filed on Dec. 19, 2014.

(51) Int. Cl.
*A61B 17/28* (2006.01)
*A61B 34/00* (2016.01)
*A61B 34/37* (2016.01)

(52) U.S. Cl.
CPC .............. *A61B 34/71* (2016.02); *A61B 34/77* (2016.02); *A61B 17/28* (2013.01); *A61B 34/37* (2016.02)

(58) Field of Classification Search
CPC ......... A61B 17/28; A61B 17/29; A61B 34/37; A61B 34/71; A61B 34/77
(Continued)

(56) References Cited

U.S. PATENT DOCUMENTS 2,764,301 A    9/1956  Goertz et al.
2,771,199 A   11/1956  Jelatis
(Continued)

FOREIGN PATENT DOCUMENTS

CN    101027010        8/2007
CN    101584594 A     11/2009
(Continued)

OTHER PUBLICATIONS

US 9,232,978 B2, 01/2016, Shellenberger et al. (withdrawn)
(Continued)

*Primary Examiner* — George J Ulsh
*Assistant Examiner* — Andrew P. Restaino
(74) *Attorney, Agent, or Firm* — Eversheds Sutherland (US) LLP; Christopher C. Bolten; Albert K. Heng

(57) ABSTRACT

Disclosed is a surgical instrument with an articulated end-effector, such as a dissector, scissor or grasper, to enhance a surgeon's performance during various surgical procedures. The longitudinal axis of the instrument is defined by a shaft, which may be inserted into a surgical incision or trocar in a body of a patient. The articulated end-effector is mounted on the distal extremity of the instrument shaft and comprises a plurality of links interconnected by a plurality of joints, whose movements are remotely actuated by the surgeon's hands. This remote actuation is accomplished through mechanical transmission, mainly along flexible elements, which are able to deliver motion from a set of actuation elements, placed at a proximal extremity of the shaft, to the instrument's articulated end-effector. The articulated end-effector further comprises one or more movement-amplification elements that amplify the movement transmitted by the flexible elements so that the movement of the proximal actuation elements can be minimized while the fatigue resistance of the instrument is maintained or increased. In
(Continued)

addition, this invention can provide short distances between the articulations of the end-effector and guaranteed simplified maintenance procedures if some moving links of the end-effector have to be removed.

18 Claims, 26 Drawing Sheets

(58) Field of Classification Search
  USPC .......................................................... 606/205
  See application file for complete search history.

(56) References Cited

U.S. PATENT DOCUMENTS

| | | |
|---|---|---|
| 2,774,488 A | 12/1956 | Goertz |
| 2,846,084 A | 8/1958 | Goertz et al. |
| 3,065,863 A | 11/1962 | Saunders, Jr. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker et al. |
| 3,425,569 A | 2/1969 | Haaker et al. |
| 4,221,516 A | 9/1980 | Haaker et al. |
| 4,756,655 A | 7/1988 | Jameson |
| 5,147,357 A | 9/1992 | Rose et al. |
| 5,176,352 A | 1/1993 | Braun |
| 5,207,114 A | 5/1993 | Salisbury et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,955 A | 7/1997 | Hashimoto et al. |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,784,542 A | 7/1998 | Ohm et al. |
| 5,792,045 A | 8/1998 | Adair |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,063,095 A | 5/2000 | Wang et al. |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 * | 5/2002 | Wallace ................ A61B 34/71 606/1 |
| 6,435,794 B1 | 8/2002 | Springer |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,799,065 B1 | 9/2004 | Niemeyer |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,602,287 B2 | 12/2013 | Yates et al. |
| 8,603,077 B2 | 12/2013 | Cooper et al. |
| 8,616,431 B2 | 12/2013 | Timm et al. |
| 8,617,203 B2 | 12/2013 | Stefanchik et al. |

(56) References Cited

U.S. PATENT DOCUMENTS

| | | |
|---|---|---|
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,860 B2 | 8/2015 | Viola et al. |
| 9,113,861 B2 | 8/2015 | Martin et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,795,282 B2 | 10/2017 | Sholev et al. |
| 9,795,454 B2 | 10/2017 | Seeber et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,052,157 B2 | 8/2018 | Frimer et al. |
| 10,064,691 B2 | 9/2018 | Beira et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 10,363,055 B2 | 7/2019 | Beira et al. |
| 10,413,374 B2 | 9/2019 | Chassot et al. |
| 10,510,447 B2 | 12/2019 | Beira et al. |
| 10,548,680 B2 | 2/2020 | Beira |
| 10,568,709 B2 | 2/2020 | Beira |
| 10,646,294 B2 | 5/2020 | Beira |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll |
| 2003/0013949 A1 | 1/2003 | Moll |
| 2003/0155747 A1 | 8/2003 | Bridges |
| 2003/0208186 A1 | 11/2003 | Moreyra |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1* | 9/2007 | Nishizawa ............ A61B 17/29 606/205 |
| 2007/0299387 A1 | 12/2007 | Williams et al. |
| 2008/0039255 A1* | 2/2008 | Jinno ................... A61B 17/062 474/148 |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 | 11/2008 | El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2010/0004508 A1 | 1/2010 | Naito et al. |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |

(56) References Cited

U.S. PATENT DOCUMENTS

| | | |
|---|---|---|
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0245643 A1 | 9/2013 | Woodard et al. |
| 2013/0245647 A1 | 9/2013 | Martin et al. |
| 2013/0282027 A1 | 10/2013 | Woodard et al. |
| 2013/0303408 A1 | 11/2013 | Indermuhle |
| 2013/0304083 A1 | 11/2013 | Kaercher et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0142018 A1 | 5/2015 | Sniffin et al. |
| 2015/0150575 A1 | 6/2015 | Hartoumbekis et al. |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0302876 A1* | 10/2016 | Teichtmann ............ A61B 34/30 |
| 2016/0374766 A1 | 12/2016 | Schuh |
| 2017/0020615 A1 | 1/2017 | Koenig et al. |
| 2017/0245954 A1 | 8/2017 | Beira |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp et al. |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |
| 2019/0133698 A1 | 5/2019 | Beira et al. |
| 2019/0239968 A1 | 8/2019 | Beira et al. |
| 2019/0328473 A1 | 10/2019 | Chassot et al. |

FOREIGN PATENT DOCUMENTS

| | | |
|---|---|---|
| CN | 101637402 A | 2/2010 |
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 0 776 739 A2 | 6/1997 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 783 643 A1 | 10/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 834 244 | 5/1960 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 A1 | 3/1982 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/025818 A1 | 3/2011 |
| WO | WO-2011/027183 A2 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/007784 A1 | 1/2013 |
| WO | WO-2013/014621 A1 | 1/2013 |
| WO | WO-2013/014621 A2 | 1/2013 |

(56) References Cited

FOREIGN PATENT DOCUMENTS

| | | |
|---|---|---|
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 | 6/2014 |
| WO | WO-2014/094718 | 6/2014 |
| WO | WO-2014/094719 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2015/175200 A1 | 11/2015 |
| WO | WO-2016/083189 A1 | 6/2016 |
| WO | WO-2016/154173 A1 | 9/2016 |
| WO | WO-2016/183054 A1 | 11/2016 |
| WO | WO-01/6189284 A1 | 12/2016 |
| WO | WO-2016/189284 A1 | 12/2016 |
| WO | WO-2017/015599 A1 | 1/2017 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |
| WO | WO-2017/134077 A1 | 8/2017 |
| WO | WO-2017/220978 A1 | 12/2017 |
| WO | WO-2018/142112 A1 | 8/2018 |
| WO | WO-2018/162921 A1 | 9/2018 |

OTHER PUBLICATIONS

Abbott, et al., "Design of an Endoluminal NOTES Robotic System," IEEE/RSJ International Conference on Intelligent Robots and Systems, San Diego, Ca, pp. 410-416 (2007).

Aesculap Surgical Technologies, Aesculap® Caiman®, Advanced Bipolar Seal and Cut Technology Brochure, 6 pages (retrieved Aug. 31, 2015).

Arata, et al., "Development of a dexterous minimally-invasive surgical system with augmented force feedback capability," IEEE/RSJ International Conference on Intelligent Robots and Systems, pp. 3207-3212 (2005).

çavuşoğlu, et al., "Laparoscopic Telesurgical Workstation," IEEE Transactions on Robotics and Automation,(15)4:728-739 (1999).

Dachs, et al., "Novel Surgical Robot Design: Minimizing the Operating Envelope Within the Sterile Field," 28th International Conference, IEEE Engineering in Medicine Biology Society, New York, pp. 1505-1508 (2006).

Dario, et al., "Novel Mechatronic Tool for Computer-Assisted Arthroscopy," IEEE Transactions on Information Technology in Biomedicine, 4(1):15-29 (Mar. 2000).

Focacci, et al., "Lightweight Hand-held Robot for Laparoscopic Surgery," IEEE International Conference on Robotics & Automation, Rome, Italy, pp. 599-604 (2007).

Guthart, et al., "The Intuitive™ Telesurgery System: Overview and Application," IEEE International Conference on Robotics & Automation, San Francisco, CA, pp. 618-621 (2000).

Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).

Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).

International Search Report & Written Opinion dated Feb. 2, 2017 in Int'l PCT Patent Appl. Serial No. PCT/IB2016/001286.

International Search Report & Written Opinion dated Jan. 18, 2013 in Int'l PCT Patent Appl Serial No. PCT/IB2012/053786.

International Search Report dated Jan. 18, 2013 in Int'l PCT Patent Appl Serial No. PCT/IB2012/053786.

International Search Report dated Mar. 23, 2012 in Int'l PCT Patent Appl Serial No. PCT/IB2011/054476.

Ishii, et al., "Development of a New Bending Mechanism and Its Application to Robotic Forceps Manipulator," IEEE International Conference on Robotics & Automation, Rome, Italy, pp. 238-243 (2007).

International Search Report & Written Opinion dated May 23, 2016 in Int'l PCT Patent Appl Serial No. PCT/IB2015/002524.

International Search Report & Written Opinion dated Mar. 30, 2015 in Int'l PCT Patent Appl Serial No. PCT/EP2015/051473.

International Search Report & Written Opinion dated Apr. 26, 2016 in Int'l PCT Patent Appl Serial No. PCT/IB2015/002512.

International Search Report & Written Opinion dated May 24, 2016 in Int'l PCT Patent Appl Serial No. PCT/IB2015/002487.

International Search Report & Written Opinion dated Jun. 10, 2016 in Int'l PCT Patent Appl Serial No. PCT/IB2015/002533.

International Search Report & Written Opinion dated Jun. 13, 2016 in Int'l PCT Patent Appl Serial No. PCT/IB2015/002493.

International Search Report & Written Opinion dated Aug. 25, 2016 in Int'l PCT Patent Appl Serial No. PCT/IB2016/000542.

International Search Report & Written Opinion dated Sep. 2, 2016 in Int'l PCT Patent Appl Serial No. PCT/IB2016/000543.

Kobayashi, et al., "Small Occupancy Robotic Mechanisms for Endoscopic Surgery," International Conference on Medical Image Computing and Computer assisted Interventions, pp. 75-82 (2002).

Mayer, et al., "The Endo[PA]R System for Minimally Invasive Robotic Surgery," IEEE/RSJ International Conference on Intelligent Robots and Systems, Sendai, Japan, pp. 3637-3642 (2004).

Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).

Nakamura, et al., "Multi-DOF Forceps Manipulator System for Laparoscopic Surgery—Mechanism miniaturized & Evaluation of New Interface," 4th International Conference on Medical Image Computing and Computer assisted Interventions (MICCAI2001), pp. 606-613 (2001).

Peirs, et al., "Design of an advanced tool guiding system for robotic surgery," IEEE International Conference on Robotics & Automation, Taipei, Taiwan, pp. 2651-2656 (2003).

Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).

Seibold, et al., "Prototype of Instrument for Minimally Invasive Surgery with 6-Axis Force Sensing Capability," IEEE International Conference on Robotics & Automation, Barcelona, Spain, pp. 496-501 (2005).

Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).

Stryker®, Endoscopy, Take a Look Around, Ideal Eyes™ FFD122 HD, Articulating Laparoscope Brochure, 2 pages (2009).

Swiss Search Report dated Jun. 4, 2012 in Swiss Patent Application No. CH 00702/12.

Tavakoli, et al., "Force Reflective Master-Slave System for Minimally Invasive Surgery," IEEE/RSJ International Conference on Intelligent Robots and Systems, Las Vegas, NV, pp. 3077-3082 (2003).

Taylor, et al., "Steady-Hand Robotic System for Microsurgical Augmentation," The International Journal of Robotics Research, 18(12):1201-1210 (1999).

www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.

(56) References Cited

OTHER PUBLICATIONS

Yamashita, et al., "Development of Endoscopic Forceps Manipulator Using Multi-Slider Linkage Mechanisms," The 1st Asian Symposium on Computer Aided Surgery—Robotic and Image-Guided Surgery, Ibaraki, Japan, 4 pages (2005).
Zeus, "Robotic Surgical System" available at http://allaboutroboticsurgery.com/zeusrobot.html.
International Search Report & Written Opinion dated Jul. 10, 2018 in Int'l PCT Patent Appl. Serial No. PCT/IB2018/053272.
Communication Relating to the Results of the Partial International Search dated May 28, 2019 in Int'l PCT Patent Appl. Serial No. PCT/IB2019/050961.
Extended European Search Report dated Mar. 18, 2020 in EP Patent Appl. Serial No. 19213231.4 (DM-1031 EP).
International Search Report & Written Opinion dated Jul. 7, 2020 in Int'l PCT Patent Appl. Serial No. PCTIB2020050039 (DM-1610 PCT).
U.S. Appl. No. 13/878,924, filed May 17, 2013.
U.S. Appl. No. 14/233,184 / U.S. Pat. No. 9,696,700, filed Jan. 16, 2014 / Jul. 4, 2017.
U.S. Appl. No. 15/116,509, filed Aug. 3, 2016.
U.S. Appl. No. 15/506,659, filed Feb. 24, 2017.
U.S. Appl. No. 15/536,539, filed Jun. 15, 2017.
U.S. Appl. No. 15/536,568, filed Jun. 15, 2017.
U.S. Appl. No. 15/536,573, filed Jun. 15, 2017.
U.S. Appl. No. 15/536,576, filed Jun. 15, 2017.
U.S. Appl. No. 15/633,611, filed Jun. 26, 2017.

\* cited by examiner

SURGICAL INSTRUMENT WITH ARTICULATED END-EFFECTOR

FIELD OF THE INVENTION

The present invention relates to the field of remotely actuated mechanical systems, more particularly to endoscopic mechanisms, and most particularly to remotely actuated endoscopic surgical instruments. More specifically, this invention relates to endoscopic articulated mechanisms such as graspers, dissectors, and scissors, wherein the orientation of end-effectors in relation to the instrument shaft is able to be controlled. Most specifically, the invention relates to such mechanisms wherein the actuation and orientation of the instrument's distal end-effector is remotely performed, and transmitted from the proximal to the distal extremity of the instrument shaft, by mechanical transmission elements. This mechanism is intended to be used primarily in surgical procedures, where the instruments with articulated end-effectors are passing through incisions or trocars into a patient's body. It is also adapted for any suitable remote actuated application requiring a dexterous manipulation with high stiffness and precision such as, but in no way limited to, assembly manipulation, manipulation in narrow places, manipulation in dangerous or difficult environments, and manipulation in contaminated or sterile environments.

BACKGROUND OF THE INVENTION

Open surgery is still the standard technique for most surgical procedures. It has been used by the medical community for several decades and consists of performing the surgical tasks by a long incision in the abdomen or other body cavity, through which traditional surgical tools are inserted. However, due to the long incision, this approach is extremely invasive for the patient, resulting in substantial blood loss during the surgery and long and painful recovery periods in an in-patient setting.

In order to reduce the invasiveness of open surgery, laparoscopy, a minimally invasive technique, was developed. Instead of a single long incision, one or more smaller incisions are made in the patient through which appropriately sized surgical instruments and endoscopic cameras are inserted. Because of the low degree of invasiveness, laparoscopic techniques reduce blood loss and pain while also shortening hospital stays. When performed by experienced surgeons, these techniques can attain clinical outcomes similar to open surgery. However, despite the above-mentioned advantages, laparoscopy requires advanced surgical skills to manipulate the rigid and long instrumentation through small incisions in the patient.

Traditionally, laparoscopic instruments, such as graspers, dissectors, scissors and other tools, have been mounted on straight shafts. These shafts are inserted through small incisions into the patient's body and, because of that, their range of motion inside the body is reduced. The entry incision acts as a point of rotation, decreasing the freedom for positioning and orientating the instruments inside the patient. Therefore, due to the drawbacks of its instrumentation, laparoscopic procedures are mainly limited to use in simple surgeries, while only a small minority of surgeons is able to use them in complex procedures.

Accordingly, there is a clear need for providing distal articulations to effector elements of laparoscopic instruments, allowing the distal effector elements to be angulated with respect to the longitudinal axis of the instrument shaft. This enables the surgeon to reach the tissue by oblique angles with respect to the longitudinal axis of the shaft. In addition, the instrument should be able to fully operate its effector elements at such angulations.

Although different articulated wrists have been proposed using rigid mechanical transmission (U.S. Pat. No. 5,330,502, U.S. Pat. No. 7,819,894, U.S. Pat. No. 7,674,255), flexible mechanical transmission is considered to exhibit better performance characteristics in terms of weight, friction and other attributes (WO9743942, U.S. Pat. No. 6,394,998, U.S. Pat. No. 6,554,844).

When metallic ropes are used with a suitable strand construction, flexible mechanical transmission can provide a fairly good axial stiffness with an acceptable radial (bending) flexibility. As a consequence, the ropes should be ideally passing around large-diameter pulleys in order to reduce the rubbing of the internal strands, the friction on the overall mechanical transmission and the wear on the ropes across several cycles of utilization.

In the cable-driven surgical instruments disclosed in WO9743942, U.S. Pat. No. 6,394,998, and U.S. Pat. No. 6,554,844 the motion on each degree-of-freedom is transmitted from the proximal hub to the distal articulation by a rotating spool, which is connected to the respective distal pulley by a single cable loop (FIG. 17). Since these spools, on the proximal hub, are independent from each other, their rotation $\theta1$, $\theta2$, $\theta3$, $\theta4$ can potentially assume any value, enabling a suitable length of cable 12, 12' to be supplied to the each distal articulation and compensate for the effects of kinematic coupling between the different cable-actuated end-effector joints. However, if the motion is transmitted from the proximal hub to each one of the distal articulations by rotating elements with non-independent range of rotation (like in the system disclosed in EP14159025—FIGS. 9 and 10), and not by an independent rotating spools, the actuating rotation of each one of the rotating elements is limited by the actuating rotation of the other rotating elements. This limitation is particularly problematic when a broad range of motion is supposed to be achieved at the distal articulations and there are dimensional constraints on the diameter of distal pulleys given the diameter and construction of the actuation ropes.

Accordingly, an aim of the present invention is to overcome the aforementioned drawbacks of the prior art by providing a new articulated end-effector, preferably to be used in a cable-driven surgical instrument, and capable of providing enough amplitude of motion to the instrument's distal articulations, especially when the amplitude of actuation rotating elements, at the proximal extremity of the instrument shaft, is limited. In addition, another aim of the present invention is to preserve the fatigue resistance of the instrument by ensuring suitable working configurations for the flexible elements composing the mechanical transmission system.

SUMMARY OF THE INVENTION

Theses aims and other advantages are achieved by a new articulated end-effector mechanism, designed to be used at the distal extremity of a surgical instrument shaft, in the form of, for example, a dissector, scissor or grasper. The shaft defines the longitudinal axis of the instrument and is able to move according to the mobility constraints imposed by a body incision, which includes a rotational movement about its own axis. This rotation also causes the rotation of the end-effector, mounted on the distal extremity of the shaft. Thus, the instrument shaft has the combined function of positioning the end-effector within the interior of the patient's body and allowing the passage of the different mechanical elements that are able to actuate the different distal end-effector articulations, by transmitting motion from an instrument hub, placed on the proximal extremity of the instrument shaft, to the distal end-effector articulations. These distal articulations of the end-effector are able to (1) operate the surgical instrument in order to accomplish its function (for example, grasping or cutting) and (2) provide orientation motions between the end effector and the instrument shaft.

The movement of each distal articulation of the end-effector is originated by the movement of a rotating element, located on the proximal hub, which is connected to a distal amplification element, placed on the instrument's end-effector, by flexible transmission elements passing through the instrument shaft. This distal amplification element is then able to transmit, and amplify, the movement to the respective end-effector link by a contact force. The amplification element is directly connected to the flexible transmission elements at a grooved geometry, having a pulley-like shape with a relatively large diameter, so that the wear of the ropes can be minimized.

In addition, this invention can provide short distances between the articulations of the end-effector and guaranteed simplified maintenance procedures if some moving links of the end-effector have to be removed.

BRIEF DESCRIPTION OF FIGURES

The invention will be better understood according to the following detailed description of several embodiments with reference to the attached drawings, in which.

DETAILED DESCRIPTION OF THE INVENTION

Figure 1:
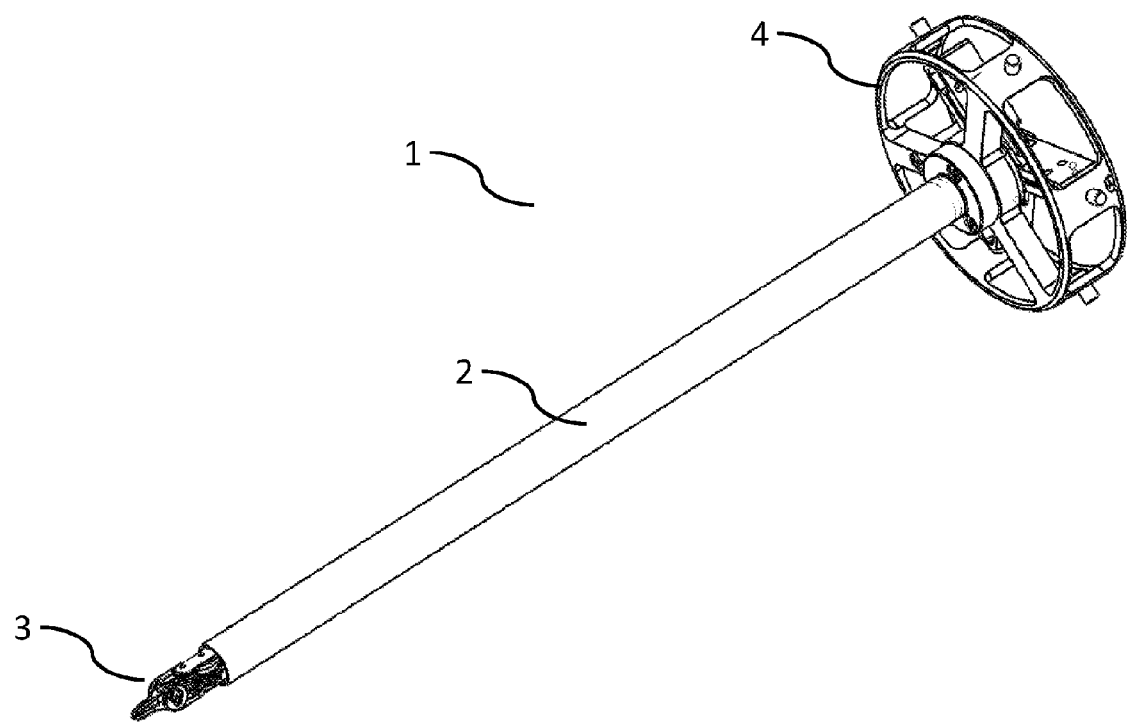
FIG. 1 shows a perspective view of a surgical instrument including an articulated end-effector according to an embodiment of the invention.
Figure 2:
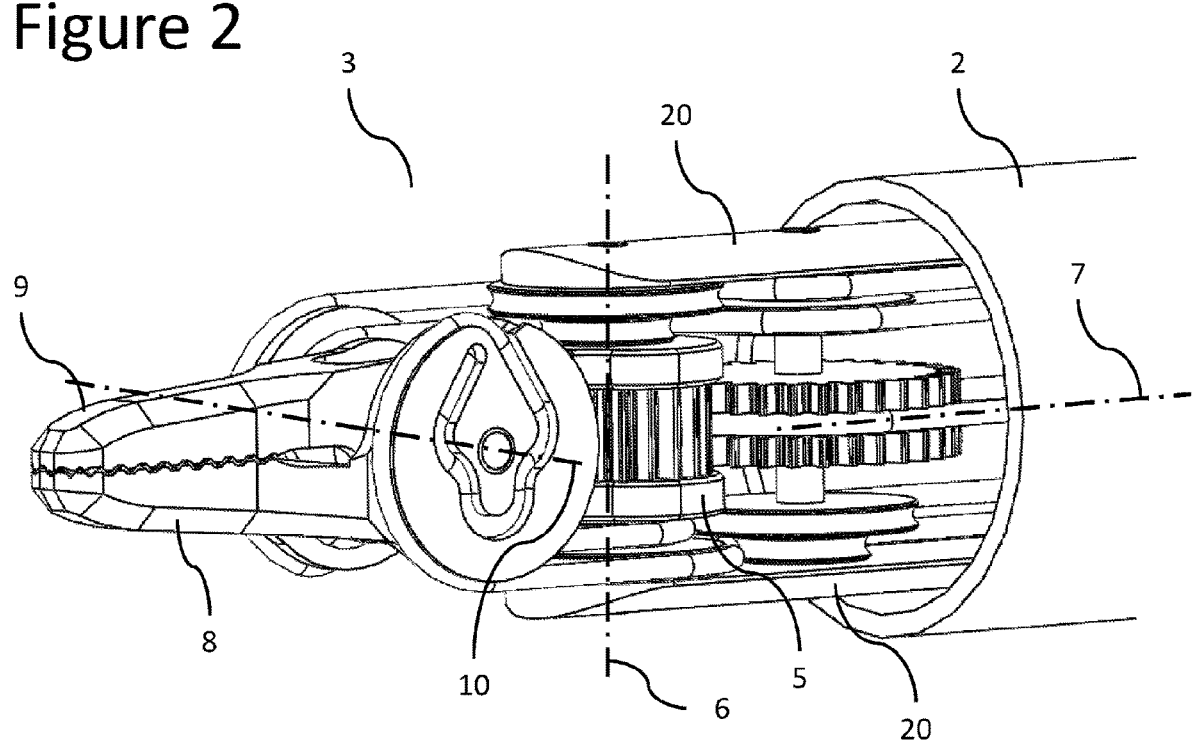
FIG. 2 shows a perspective view of the articulated end-effector of the surgical instrument according to an embodiment of the invention.

A surgical instrument 1 for minimally invasive surgical procedures, with an articulated end-effector constructed in accordance with an embodiment of the present invention, is described herein, and is seen generally in FIG. 1. This instrument 1 includes a main shaft 2, a distal end-effector 3 and a proximal hub 4. Referring to FIG. 2, the end-effector 3 is connected to the distal extremity 20 of the main shaft 2 by a proximal joint, which allows the rotation of the proximal end-effector link 5 by the proximal axis 6 in such a manner that the orientation of the proximal end-effector link 5 with respect to the main shaft axis 7 can be changed.

Referring to FIG. 2, the distal end-effector links 8, 9 are rotatably connected to the proximal end-effector link 5 by two distal joints, having coincident axes of rotation, which are represented by the distal axis 10. This distal axis 10 is substantially perpendicular and non-intersecting with the proximal axis 6 and substantially intersects the main shaft axis 7.

Figure 3:
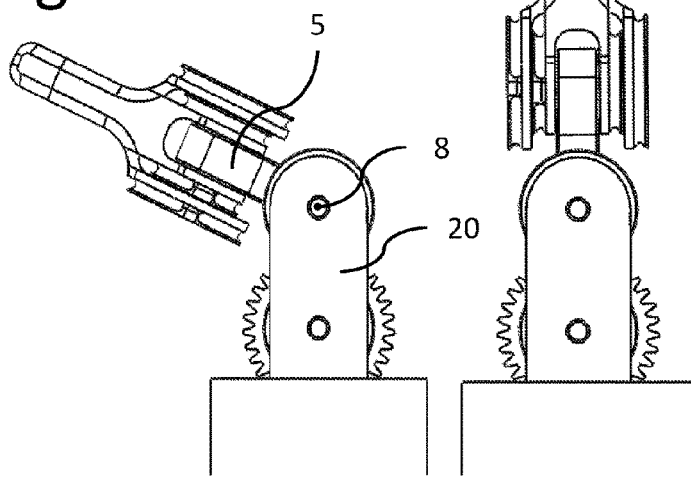
FIG. 3 shows the articulated end-effector of FIG. 2 in a first active position.
Figure 4:
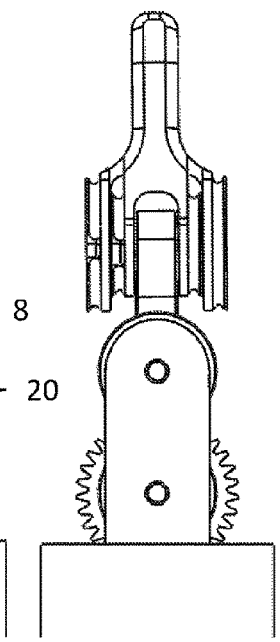
FIG. 4 shows the articulated end-effector of FIG. 2 in a second active position.
Figure 5:
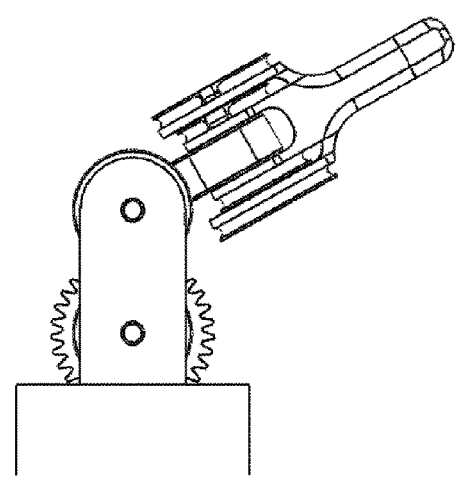
FIG. 5 shows the articulated end-effector of FIG. 2 in a third active position.

By actuating the proximal joint, the proximal end-effector link 5 can be angulated over the proximal axis 6, with respect to the plane containing the main shaft axis 7 and the proximal axis 6, substantially up to ±90°. FIGS. 3 and 5 show the surgical instrument 1 with different angular displacements at the proximal joint.

Figure 6:
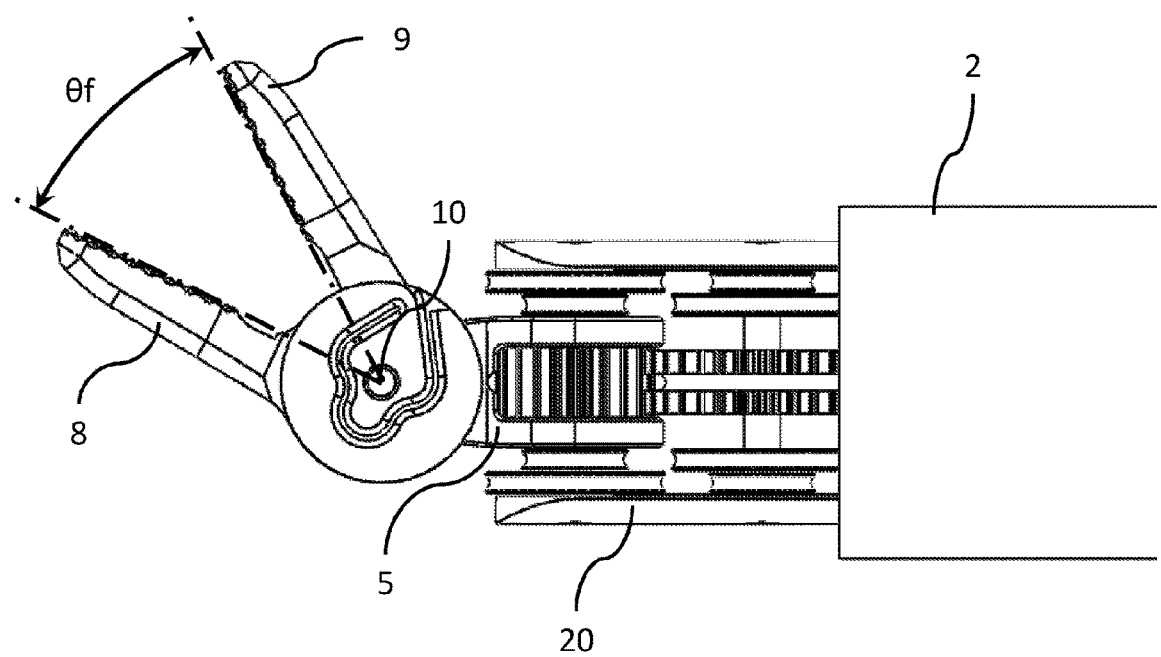
FIG. 6 shows the articulated end-effector of FIG. 2 in a fourth active position.
Figure 7:
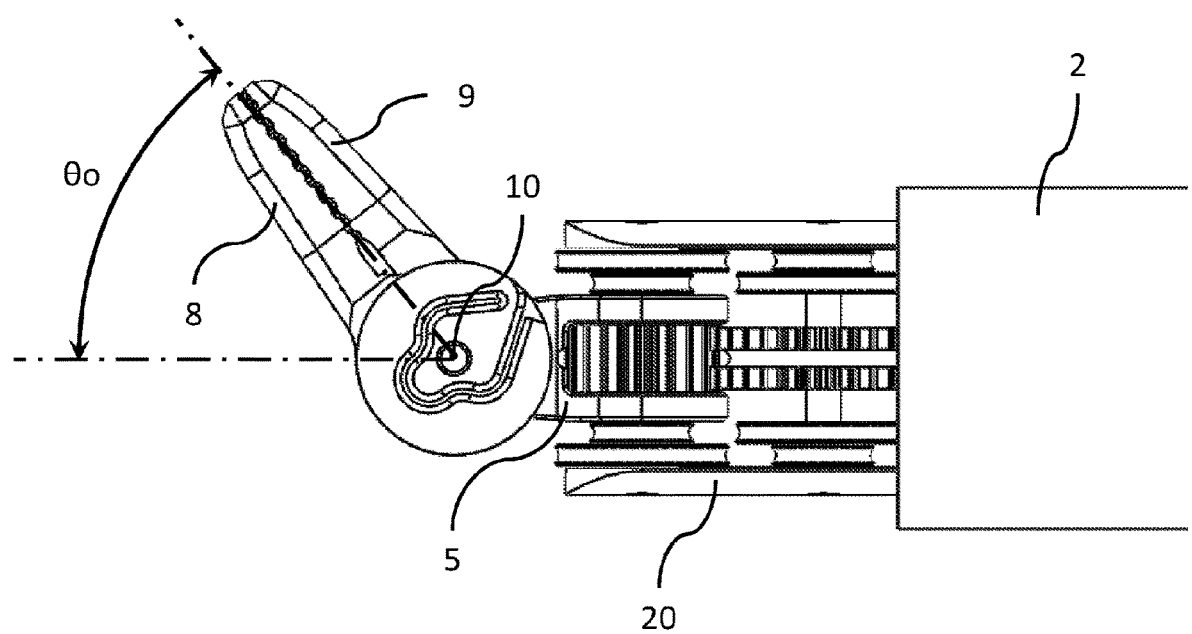
FIG. 7 shows the articulated end-effector of FIG. 2 in a sixth active position.

By actuating the two distal joints, the two distal end-effector links 8, 9 can be angulated, over the distal axis 10, with respect to the plane containing the main shaft axis 7 and the distal axis 10, substantially up to ±90°. Consequently, by the combination of rotations of the two distal end-effector links, it is possible to operate the surgical instrument, θf, in order to accomplish its function (FIG. 6) and to provide orientation motions, θo, between the end effector and the instrument shaft (FIG. 7).

Figure 8:
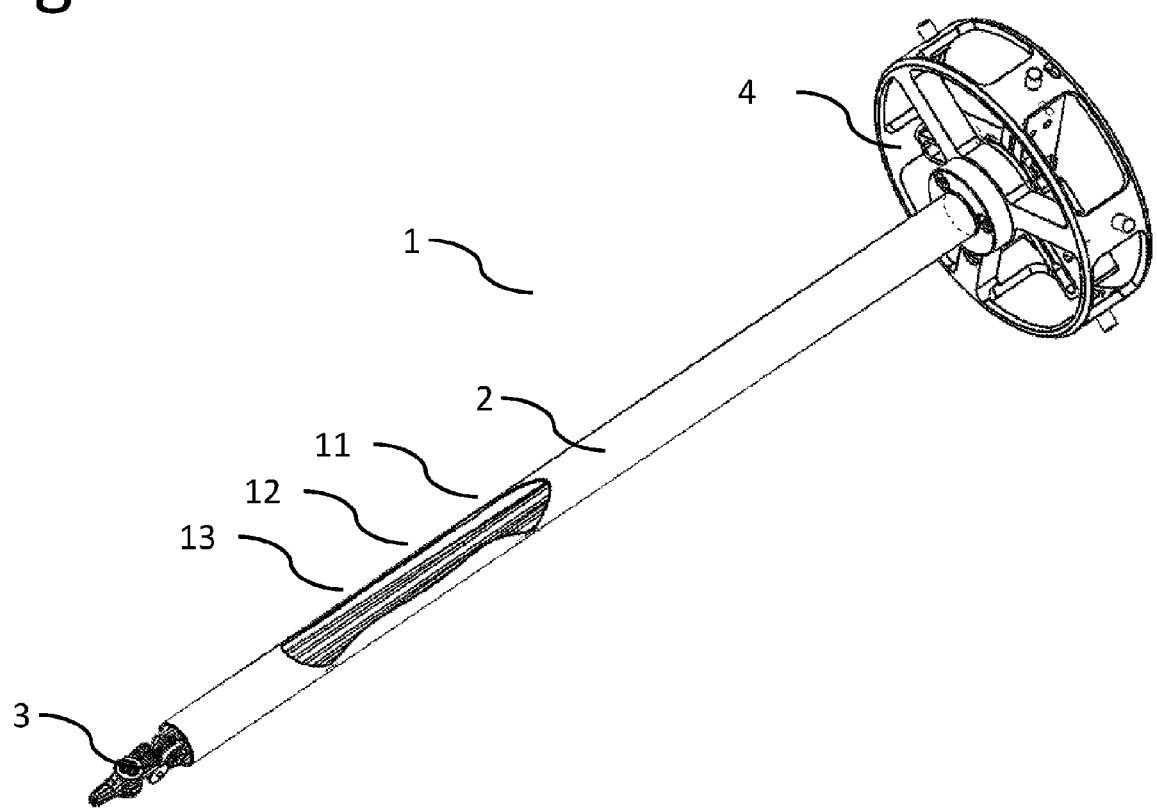
FIG. 8 shows a perspective view of the surgical instrument of FIG. 1 with a schematic cutout of an outer tube of the longitudinal shaft of the surgical instrument, through which is it possible to see the different flexible mechanical transmission elements.

With reference to FIG. 8, the main shaft 2 allows the passage of flexible elements 11, 12, 13 that are able to deliver motion to the different end-effector links 5, 8, 9, from the proximal hub 4 at the proximal extremity of the instrument.

Figure 9:
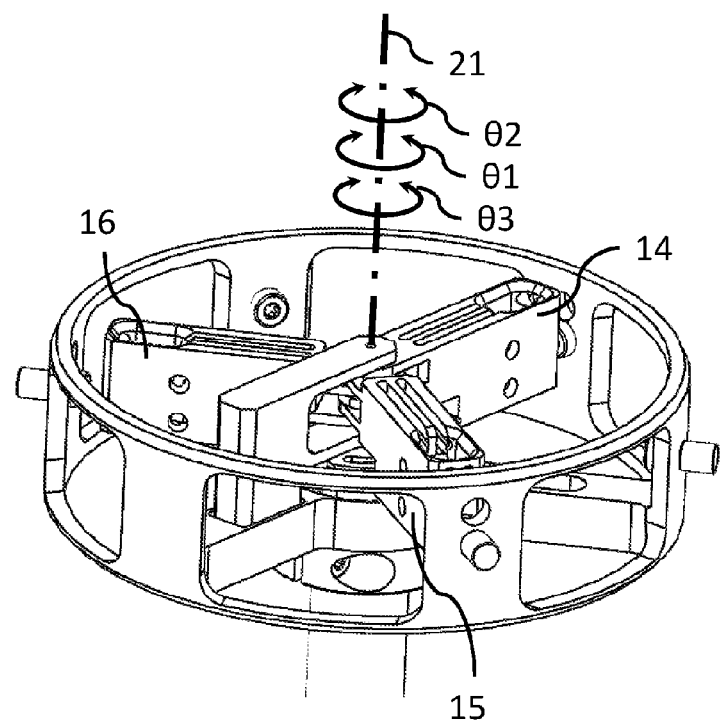
FIG. 9 shows a perspective view of the proximal hub with the different proximal rotating elements.
Figure 10:
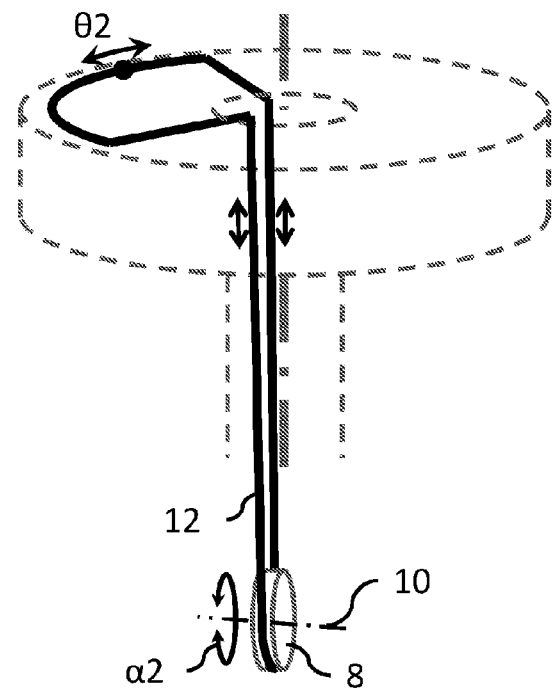
FIG. 10 shows the simplified path of a flexible transmission element actuating a distal articulation of the end-effector.

With reference to FIGS. 9 and 10, the movement is transmitted to each one of the three distal articulations of the instrument by a rotating element 14, 15, 16, which is able to rotate about an axis 21 and is connected to a cable loop 11, 12, 13. As a result, when the rotating element 14, 15, 16 rotates a certain angle θ1, θ2, θ3 about the axis 21, a rotation α1, α2, α3 is transmitted to the respective end-effector member 5, 8, 9.

Figure 11:
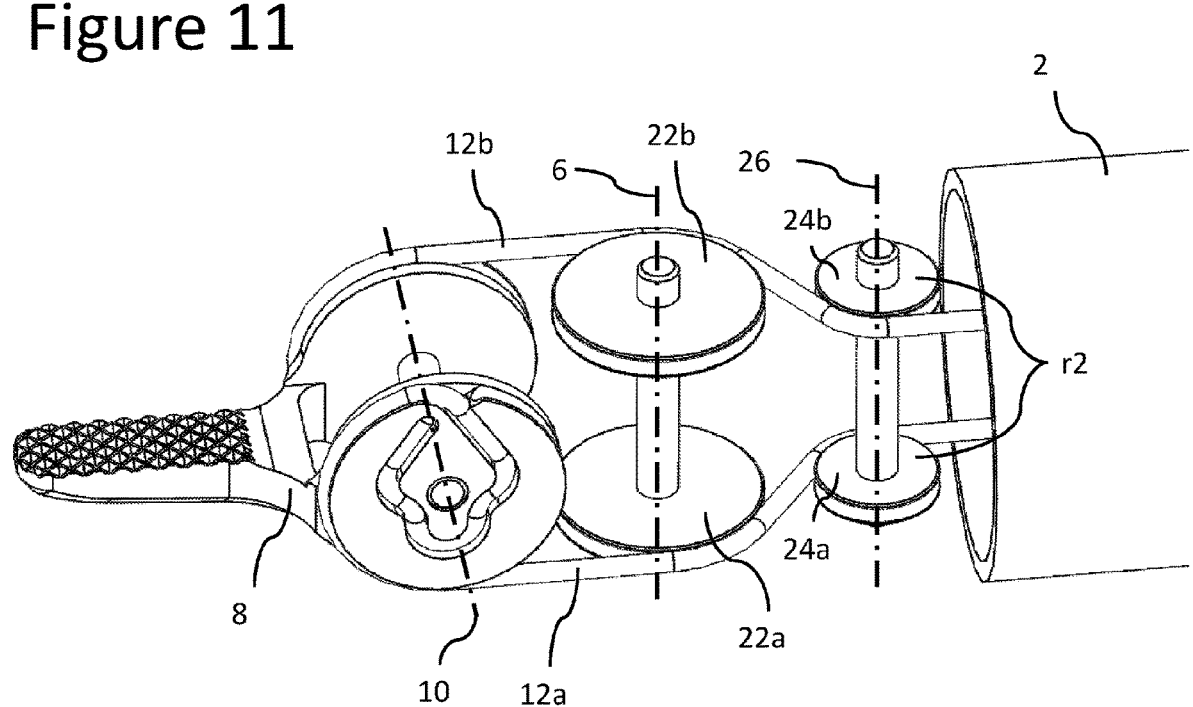
FIG. 11 shows the actuation topology for a first distal end-effector link.
Figure 12:
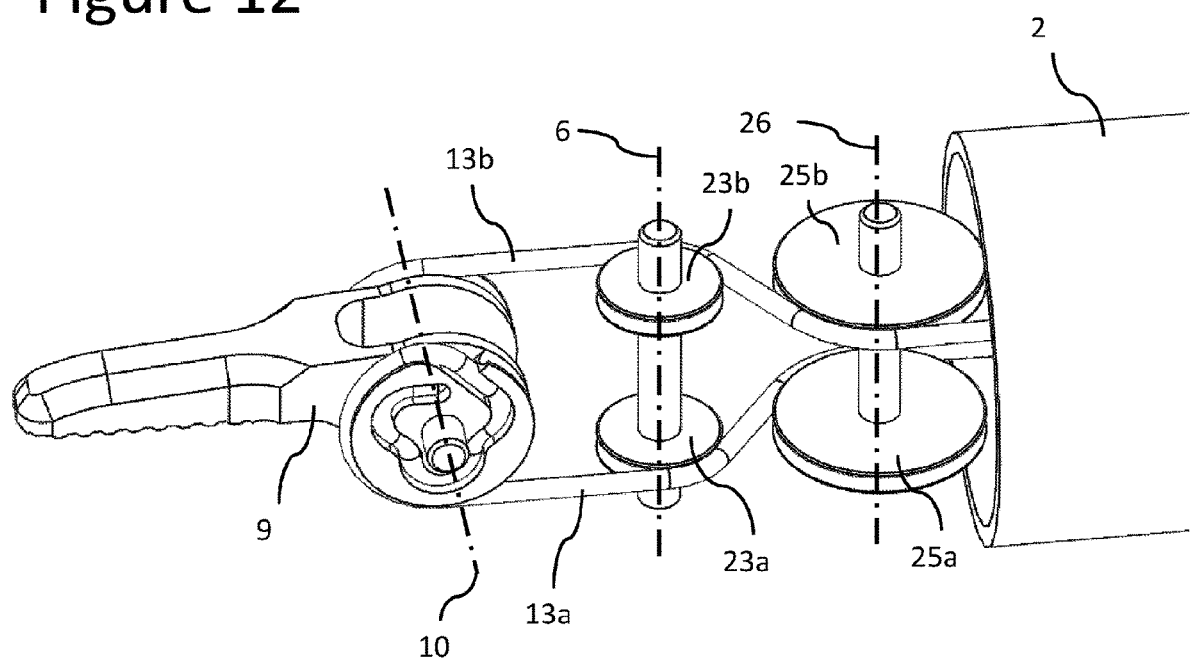
FIG. 12 shows the actuation topology for a second distal end-effector link.
Figure 13:
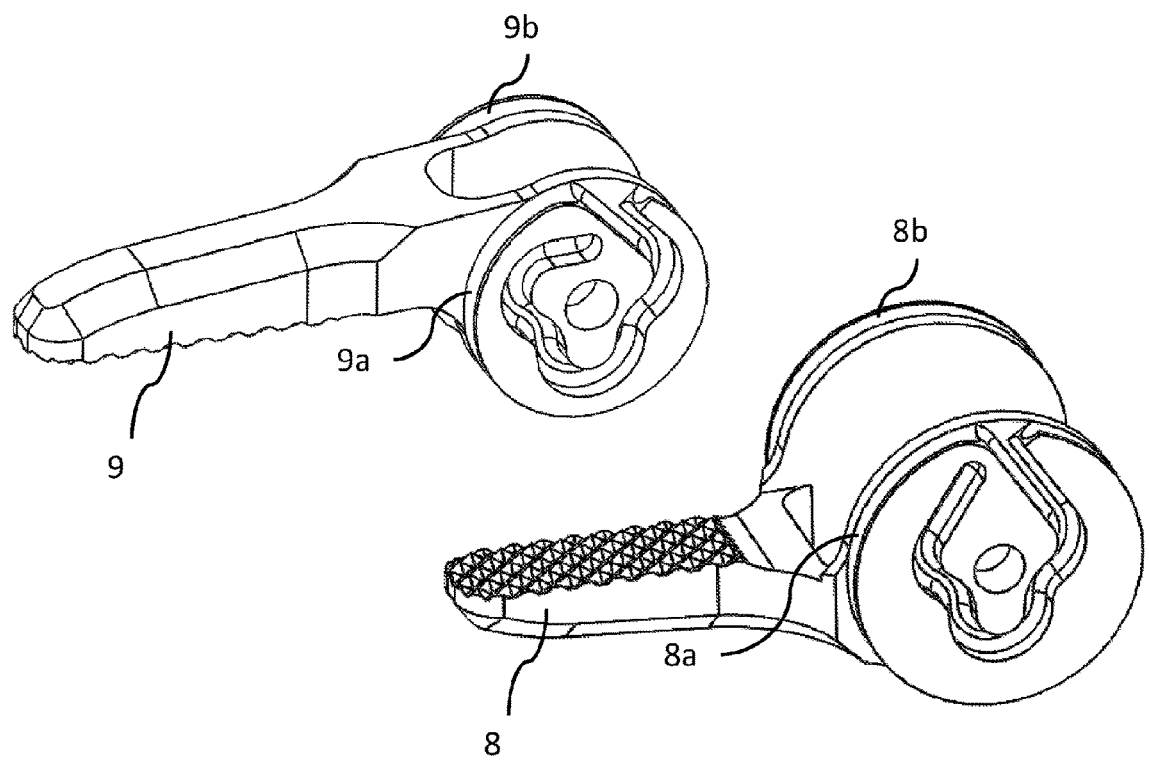
FIG. 13 shows a perspective views of the two distal end-effector links.

As can be seen in FIGS. 11 and 12, the distal end-effector members 8, 9 are operatively connected to flexible members 12 and 13 so that they can be independently rotated in both directions along the distal axis 10. The contact between the flexible elements and the distal end-effector elements is made in the circular grooved surfaces 8a, 8b, 9a, 9b (FIG. 13), which have a pulley-like geometry. Each one of the flexible elements 12, 13 is composed by two different segments, 12a, 12b, 13a, 13b, which form a closed cable loop between the respective end-effector member 8, 9 and the rotating element 15, 16. In order to keep the overall length of these closed cable loops constant, independently of the position of the end-effector member 5 around the axis 8, cable segments 12a, 12b, 13a, 13b are respectively passing through the idle pulleys 22a, 22b, 23a, 23b, which are concentric with the axis 6 of the first end-effector joint. The permanent contact between cable segments 12a, 12b, 13a, 13b and the idle pulleys 22a, 22b, 23a, 23b is guaranteed by the proximal pulleys 24a, 24b, 25a, 25b, which are concentric with the proximal axis 26.

Figure 14:
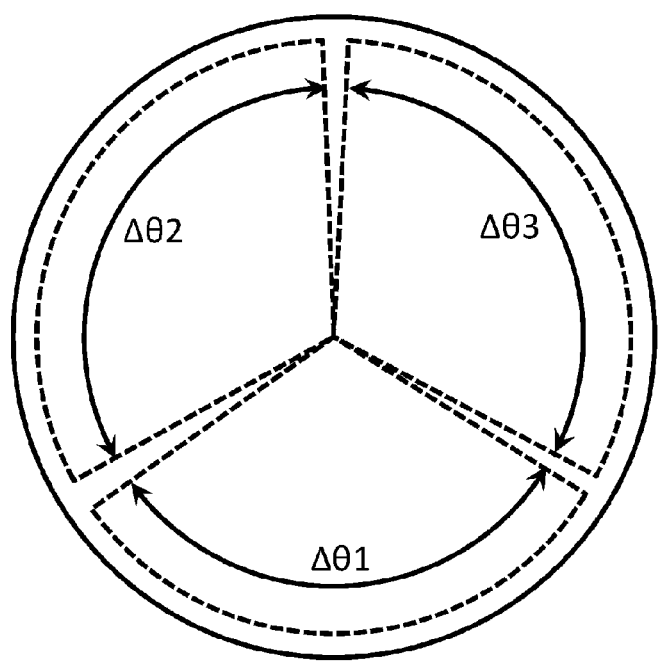
FIG. 14 shows a schematic view of the range of motion of the three rotating elements on the proximal hub of the surgical instrument.

The above mentioned transmission configuration, using idle pulleys on axis 6, increases the length of cable that needs to be supplied to actuate the distal end-effector members 8, 9 at their full range of motion. Therefore, referring to FIG. 14, the amplitudes of rotation $\Delta\theta2$, $\Delta\theta3$ that have to be reached by the rotating elements 15, 16 need to be maximized. Knowing that $\Delta\theta1+\Delta\theta2+\Delta\theta3<360°$, one can only maximize $\Delta\theta2$ and $\Delta\theta3$ by minimizing $\Delta\theta1$. To achieve this minimization, the diameter of the circular grooved surfaces in the end-effector element 5 could be simply reduced, reducing the need of cable supply for the same range of motion. However, this smaller diameter would result in worse fatigue resistance for the instrument, because the same the flexible rope would suffer a smaller-diameter bending.

Figure 15:
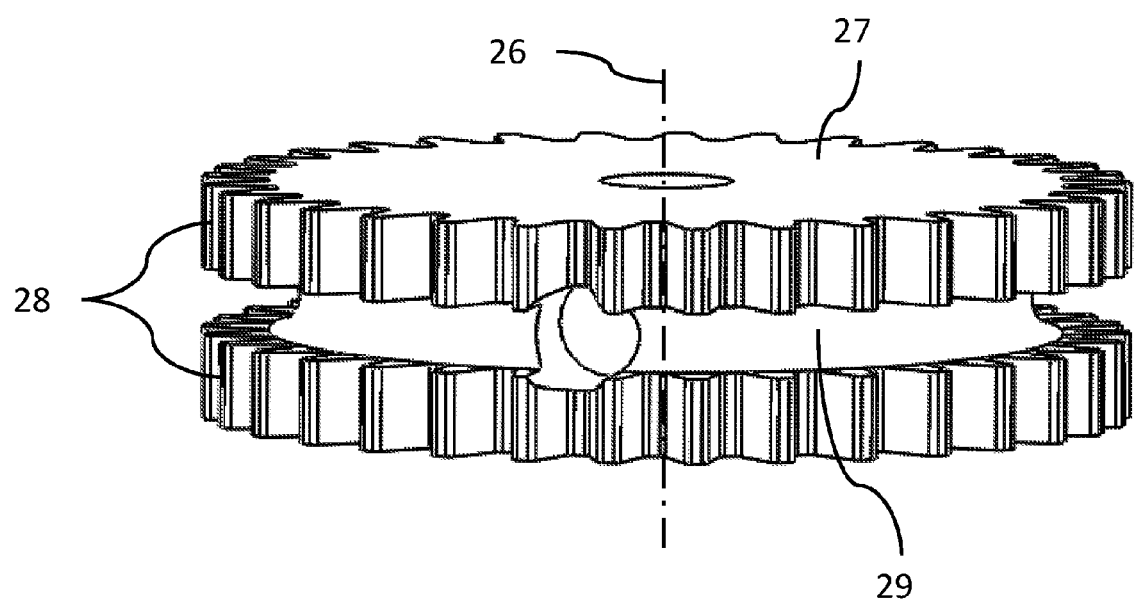
FIG. 15 shows a perspective view of the amplification element actuating the proximal end-effector link.
Figure 16:
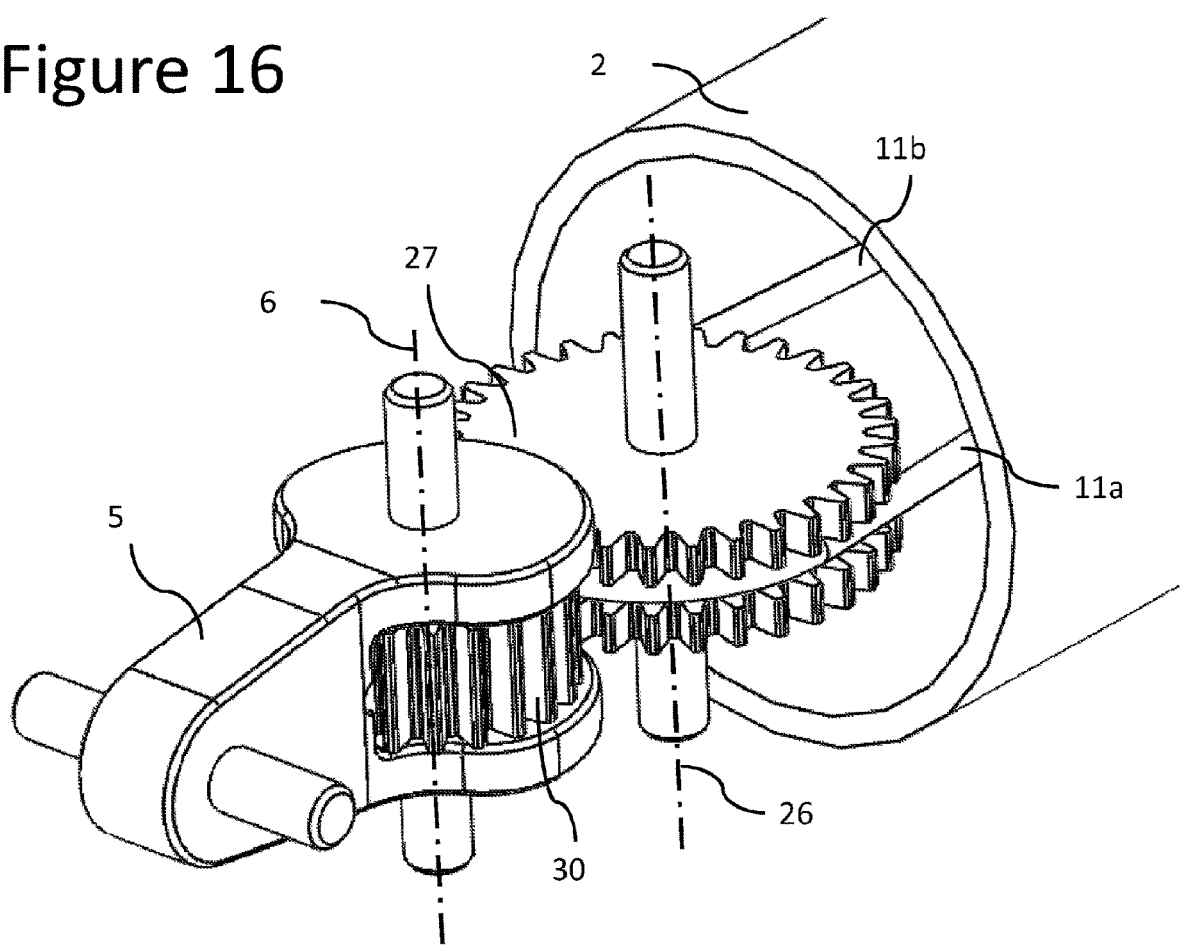
FIG. 16 shows the actuation topology for the proximal end-effector link.
Figure 17:
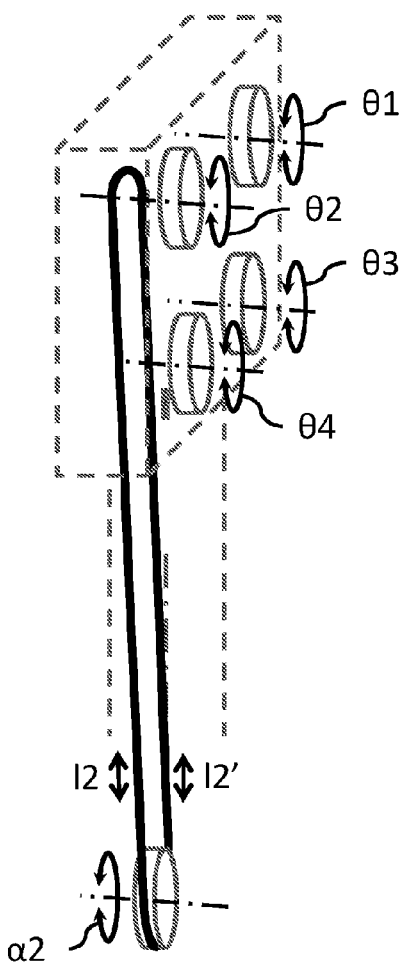
FIG. 17 shows the simplified path of a flexible transmission from a proximal rotating spool to a distal articulation of the end-effector.

In order to ameliorate these issues, and with reference to this embodiment, a distal amplification element 27 (FIG. 15) is used at the instrument's end-effector. Geometrically it consists of a disk-like element with two teeth areas 28 separated by a circular groove 29, which works as a pulley where both segments 11a, 11b of flexible element 11 are attached. As shown in FIG. 16, it is placed proximally to the end-effector element 5, being able to rotate about the proximal axis 26 (in the present embodiment). In this way, when the rotating element 14 rotates a certain angle $\theta1$ about the axis 21, a rotation $\alpha1'$, is transmitted to the distal the amplification element 27. Then, through a contact force (using teeth or other method to increase contact forces), a rotation $\alpha1$ is transmitted to a second disk-like element 30, which is attached to the end-effector element 5, with a certain amplification scale (and inverted direction) over $\alpha1'$.

Figure 18:
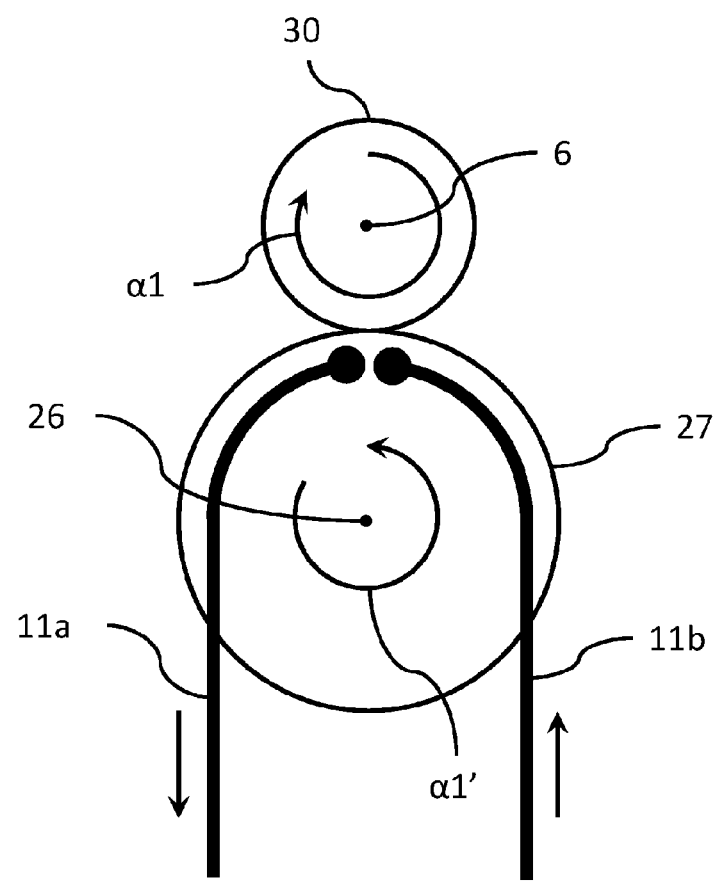
FIGS. 18 through 22 show transmission to the end effector link by rotation of an amplification element by various mechanical means.
Figure 19:
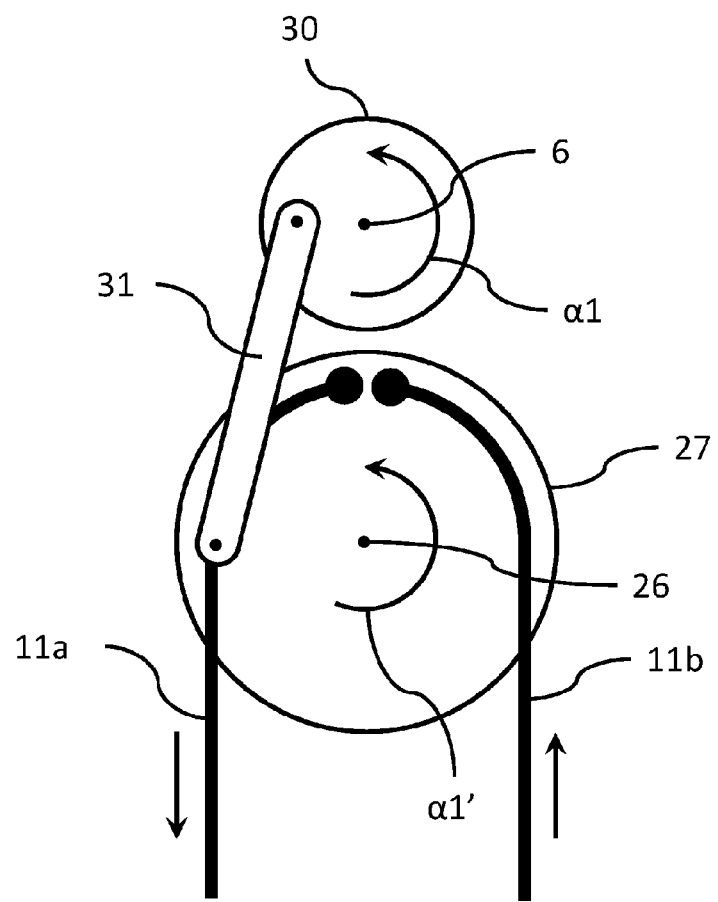
Figure 20:
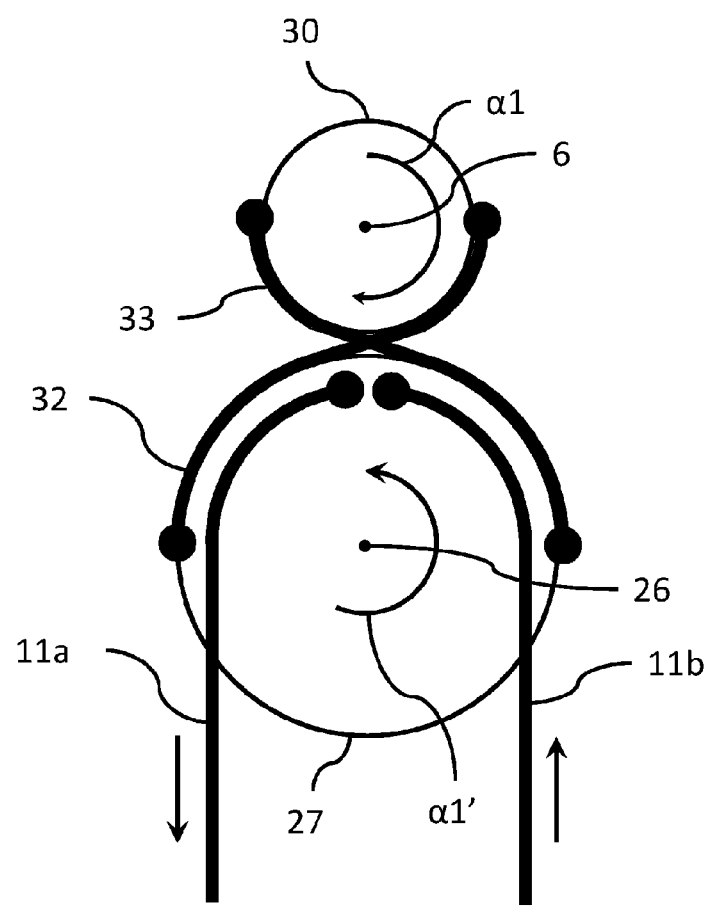
Figure 21:
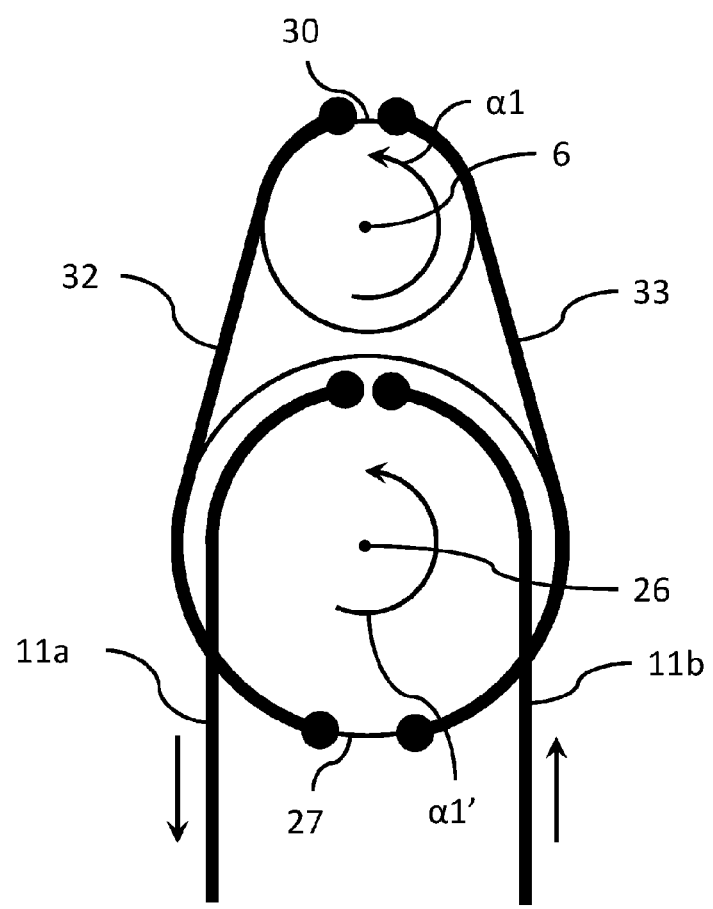
Figure 22:
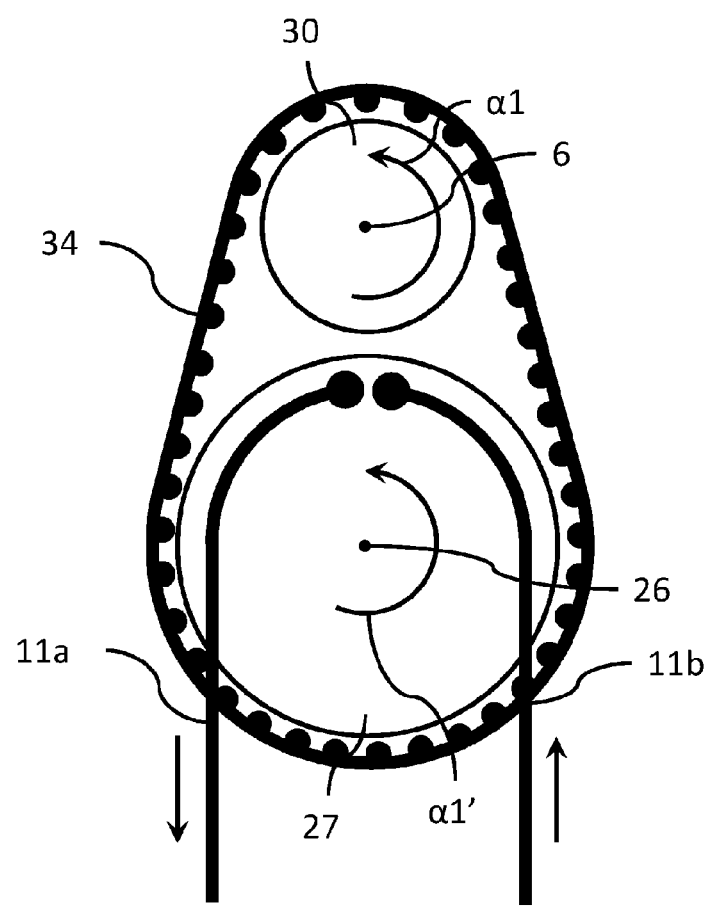

In other embodiments, the rotation $\alpha1$ can be transmitted to the element 30 (and therefore to the end-effector link 5) from the rotation $\alpha1'$ of the amplification element 27 by different mechanical solutions (FIGS. 18 to 22). In the embodiment of FIG. 18, the motion transmission is made by the friction force between the amplification element 27 and to the disk-like element 30. In the embodiment of FIG. 19, the motion transmission is made by a push-pull element 31, which is pivotally connected to the amplification element 27 and to the disk-like element 31. In still further embodiments, the motion transmission is made by two flexible elements 32, 33 whose extremities are fixed to the amplification element 27 and to the disk-like element 30 in a crossed (FIG. 20) and uncrossed (FIG. 21) configuration. In the embodiment of FIG. 22, the motion transmission is made by constant-pitch element 34 (which can take the form of a timing belt, a chain or a bead chain) that can engage the amplification element 27 and the disk-like element 30.

Given the fact that the disk elements 30 do not need to cover 360°, the embodiments of the current invention are able to provide shorter offsets between the axes 6 and 10. In addition, they further guarantee an easier maintenance procedure in case the distal components of the end-effector 3 have to be removed because the end-effector member 5 can be removed without the need to remove elements 11a and 11b.

Figure 23:
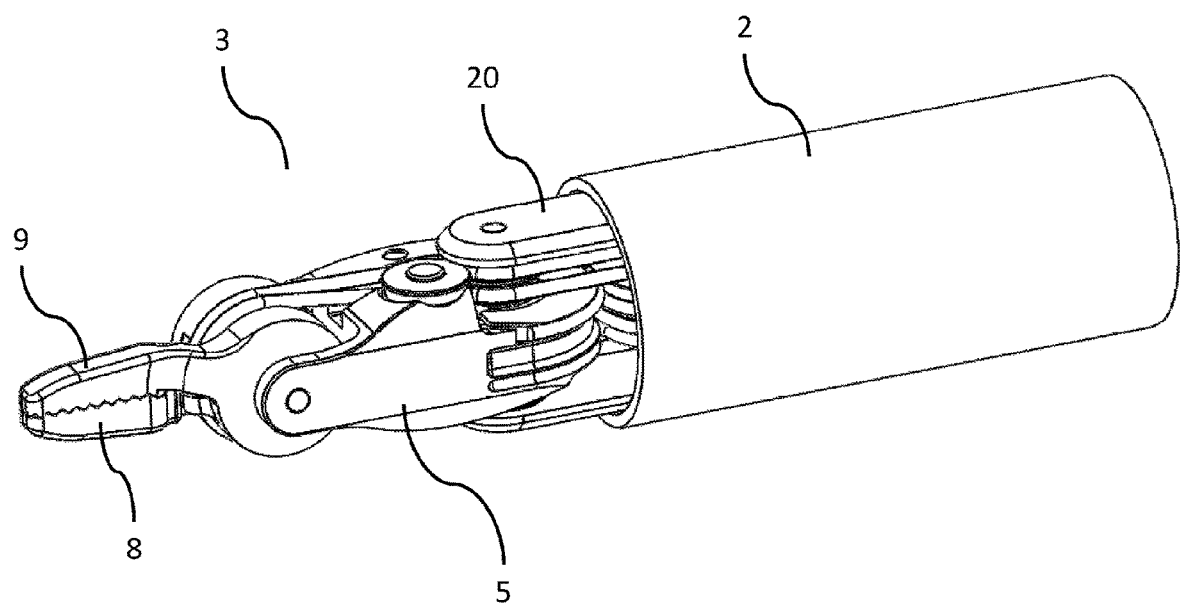
FIGS. 23 through 28 show multiple perspective views of an additional embodiment of the current invention incorporating rotation of an amplification element.
Figure 24:
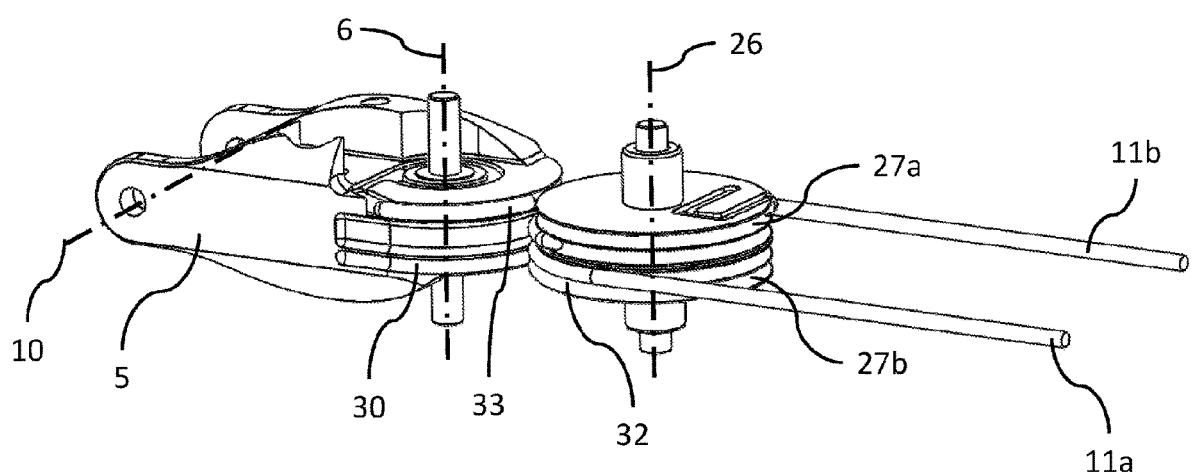
Figure 25:
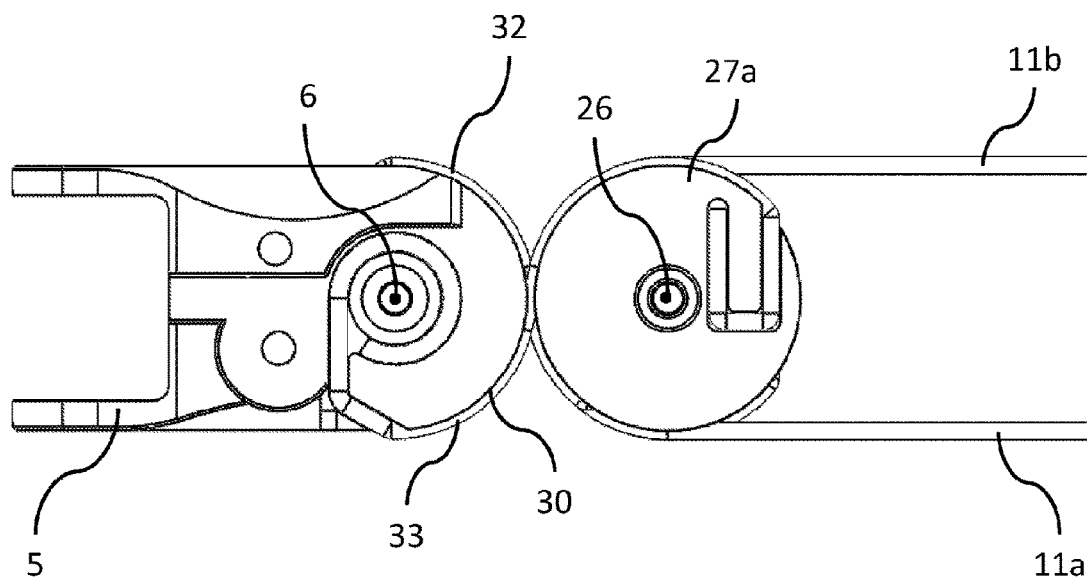
Figure 26:
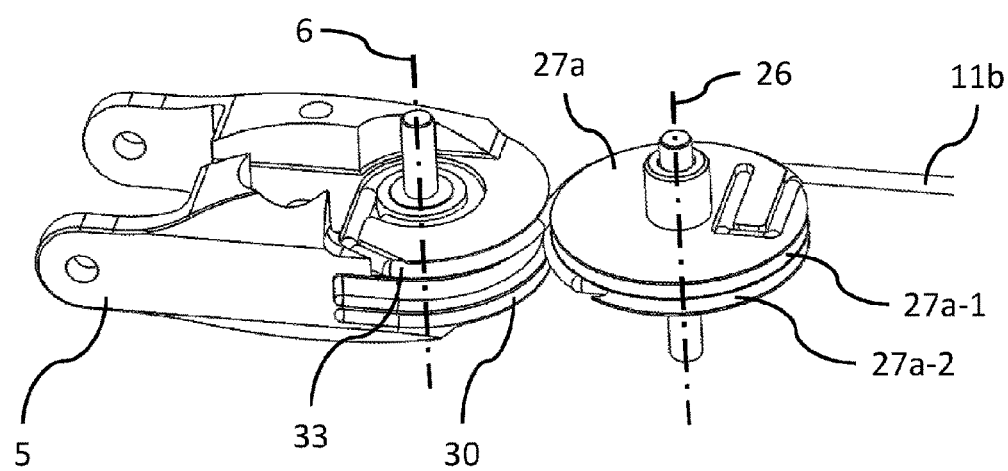
Figure 27:
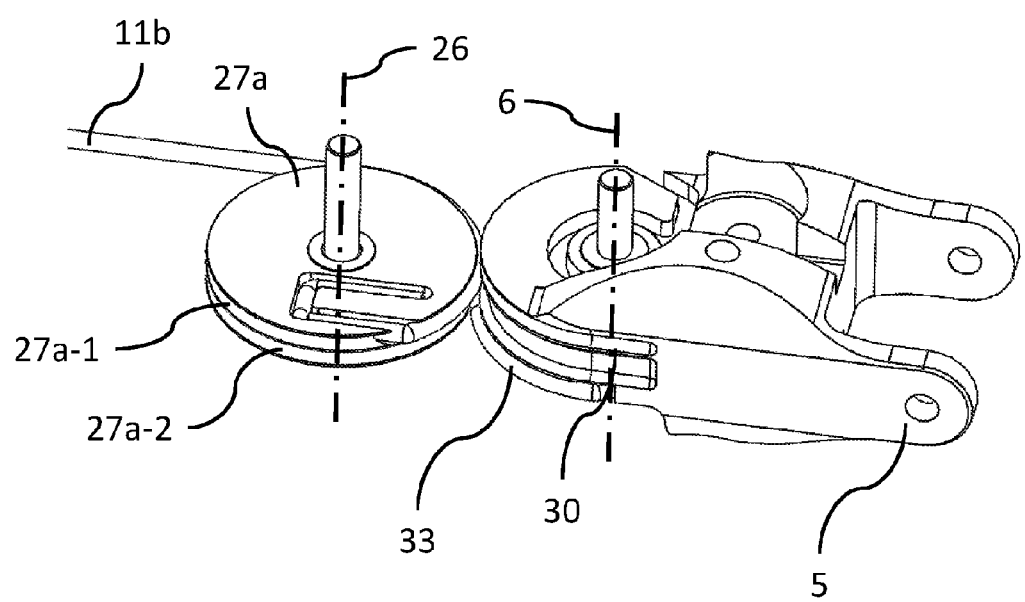
Figure 28:
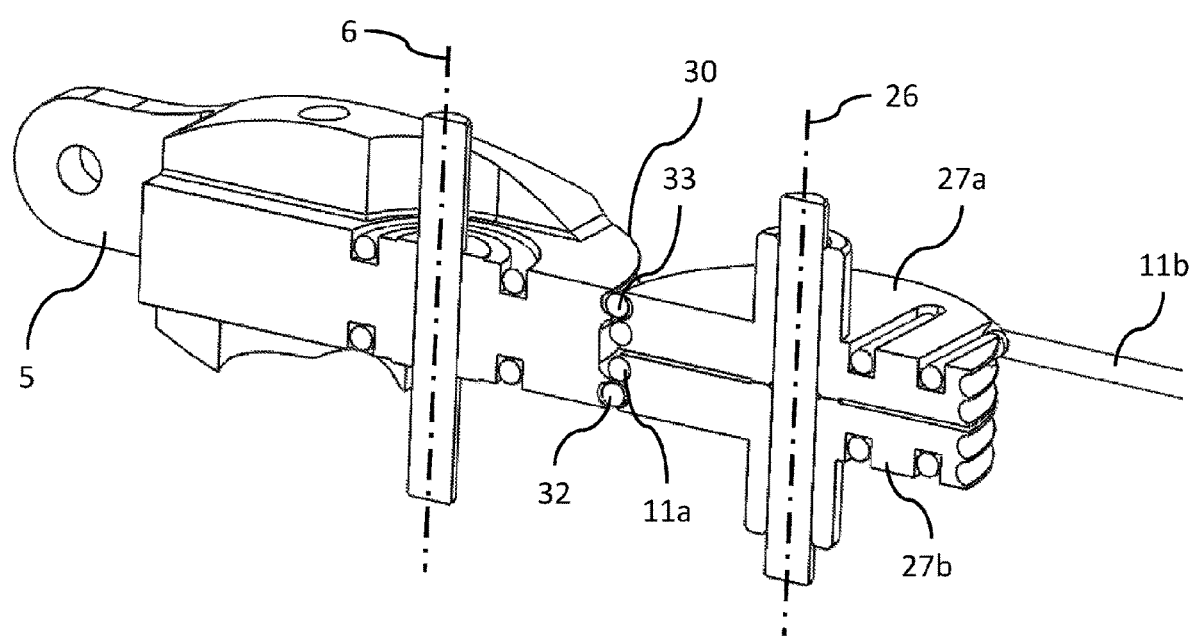

FIG. 23 shows another embodiment of the current invention (a variation of the embodiment of FIG. 20), whose components are further shown in detail in FIGS. 24 to 28. In this embodiment the distal amplification element 27 is split in two identical parts 27a, 27b, which are able to turn around the proximal axis 26. Each one of these identical parts 27a, 27b is attached to a flexible element 11b, 11a that is coming from the proximal area of the instrument. With reference to FIGS. 26 and 27, one can see that the flexible element 11b engages the circular groove 27a-2 of the identical part 27a, while the circular groove 27a-1 is filed by the flexible element 33 that is attached to the pulley-grooved surface 30 of the end-effector member 5. Therefore, the simultaneous actuation of the flexible elements 11a and 11b triggers the rotations of the identical parts 27a and 27b, around the proximal axis 26, which generates the rotation of the end-effector member 5 around the axis 6 by the action of the flexible elements 32 and 33. Different movement amplification ratios can be achieved by this system, by using different diameters on the pulley-grooved surfaces 27a-1, 27a-2 (27b-1, 27b-2) and 30.

While this invention has been particularly shown and described with reference to particular embodiments thereof, it will be understood by those skilled in the art that various changes in form and details may be made therein without departing from the spirit and scope of the invention as defined by the appended claims. For instance, the method to increase contact forces between the amplification element and the end-effector link might be changed. In addition, while in the currently shown embodiments, the proximal end-effector link is actuated by an amplification element, in other embodiments the distal end-effector elements may also be actuated by distal amplification elements according to similar principles of operation.

The invention claimed is:

1. An articulated instrument comprising:
   an instrument tube defining the longitudinal axis of the instrument and configured to accommodate flexible transmission elements;
   an articulated end-effector at a distal extremity of the instrument tube, comprising two distal end-effector links, a proximal end-effector link directly coupled to at least one of the distal end-effector links, and at least two rotation joints;
   an actuator placed at a proximal extremity of the instrument tube, configured to actuate the proximal and distal end-effector links of the articulated end-effector;
   flexible transmission elements, passing through the instrument tube, configured to transmit motion from the actuator to the end-effector links of the articulated end-effector; and
   an amplification element directly coupled to at least one of the flexible transmission elements and to the proximal end-effector links, and configured to amplify the motion transmitted from the actuator to the end-effector links of the articulated end-effector.

2. The articulated instrument of claim 1, wherein an actuation movement transmitted by the flexible transmission elements to the amplification element may be transmitted with some degree of amplification or reduction to the end-effector links.

3. The articulated instrument of claim 2, wherein the motion transmission from the amplification element to the end-effector links is made through a contact force.

4. The articulated instrument of claim 3, wherein the contact force is increased by the use of a geared geometry on the proximal end-effector links and the amplification element.

5. The articulated instrument of claim 2, wherein the proximal end-effector link comprises at least one rigid element.

6. The articulated instrument of claim 1, wherein the flexible transmission elements comprise elements with a flexible mechanical construction, selected from the group consisting of strings, ropes, belts and chains.

7. The articulated instrument of claim 1, wherein the actuator is placed on a proximal articulated handle configured to be directly controlled by the hand of a user, so that user movements are transmitted to the articulated end-effector.

8. The articulated instrument of claim 1, wherein the proximal extremity of the instrument tube is configured to be attached to a mechanical platform, so that the instrument tube is integrated as part of a master-slave telemanipulator, having the input motion of the actuators given by the movement of a proximal articulated handle.

9. The articulated instrument of claim 1, wherein the proximal extremity of the instrument tube is configured to be removeably attached to a mechanical platform, so that the instrument tube is removably integrated as part of a master-slave telemanipulator.

10. The articulated instrument of claim 1, wherein the proximal extremity of the instrument tube is configured to be attached to a robotic platform, so that it is integrated as part of a master-slave robotic telemanipulator, having the input motion of the actuator given by the movement of a proximal articulated handle.

11. The articulated instrument of claim 1, wherein the amplification element transmits amplified motion from the actuator to the proximal end-effector link of the articulated end-effector via contact force between the amplification element and the proximal end-effector link.

12. The articulated instrument of claim 11, wherein rotation of the amplification element transmits amplified motion from the actuator to the proximal end-effector link of the articulated end-effector via contact force between the amplification element and the proximal end-effector link.

13. The articulated instrument of claim 11, wherein the amplification element comprises a curved surface which contacts the proximal end-effector link of the articulated end-effector to transmit amplified motion from the actuator to the proximal end-effector link of the articulated end-effector.

14. The articulated instrument of claim 1, wherein the amplification element comprises two identical parts rotatable about a common axis, each identical part directly coupled to one of the flexible transmission elements.

15. A method for remotely actuating an articulated instrument, the method comprising: actuating an actuator to transmit motion from the actuator to proximal and distal end- effectors links of an articulated end-effector via flexible transmission elements, the proximal end-effector link directly coupled to at least one of the distal end-effector links, wherein motion transmitted from the actuator to the end-effector links is amplified via an amplification element directly coupled to at least one of the flexible transmission elements and to the proximal end-effector link.

16. The method of claim 15, wherein the flexible transmission elements extend from the actuator through an instrument tube defining the longitudinal axis of the instrument to the amplification element.

17. The method of claim 15, wherein the actuator is placed on a proximal articulated handle, and wherein actuating the actuator comprises controlling the proximal articulated handle via a hand of a user to transmit user movements to the articulated end-effector.

18. The method of claim 15, wherein motion transmitted from the actuator to the end-effector links is amplified via a contact force between the amplification element and the proximal end-effector link.

* * * * *